United States Patent
Jester et al.

(10) Patent No.: US 8,678,642 B2
(45) Date of Patent: Mar. 25, 2014

(54) METHOD FOR MRI COMPATIBLE MEDICAL DEVICE TEMPERATURE MONITORING

(71) Applicant: Imricor Medical Systems, Inc., Burnsville, MN (US)

(72) Inventors: Steven J. Jester, Eden Prairie, MN (US); Gregg S. Stenzel, Victoria, MN (US); Steven R. Wedan, Savage, MN (US); Peter Gabrail, Minneapolis, MN (US)

(73) Assignee: Imricor Medical Systems, Inc., Burnsville, MN (US)

( * ) Notice: Subject to any disclaimer, the term of this patent is extended or adjusted under 35 U.S.C. 154(b) by 0 days.

(21) Appl. No.: 13/651,007

(22) Filed: Oct. 12, 2012

(65) Prior Publication Data

US 2013/0039384 A1 Feb. 14, 2013

Related U.S. Application Data

(63) Continuation of application No. 13/202,691, filed as application No. PCT/US2010/026225 on Mar. 4, 2010.

(60) Provisional application No. 61/157,471, filed on Mar. 4, 2009.

(51) Int. Cl.
*G01K 15/00* (2006.01)
*G01J 5/00* (2006.01)
*G01K 11/00* (2006.01)

(52) U.S. Cl.
USPC .................................. 374/1; 374/131; 374/161

(58) Field of Classification Search
USPC ............................................ 374/131, 1, 161
See application file for complete search history.

(56) References Cited

U.S. PATENT DOCUMENTS

| | | | |
|---|---|---|---|
| 6,024,488 A | 2/2000 | Wu et al. | |
| 7,077,566 B2 | 7/2006 | Rajendran et al. | |
| 7,344,528 B1 | 3/2008 | Tu et al. | |
| 7,350,972 B2 | 4/2008 | Seebacher et al. | |
| 7,389,011 B2 | 6/2008 | Ogura et al. | |
| 2002/0041724 A1 | 4/2002 | Ronnekleiv et al. | |
| 2002/0147394 A1 | 10/2002 | Ellingsen | |
| 2003/0050557 A1 | 3/2003 | Susil et al. | |
| 2006/0011820 A1 | 1/2006 | Chow-Shing et al. | |
| 2006/0146909 A1 | 7/2006 | Morse et al. | |

(Continued)

OTHER PUBLICATIONS

First Office Action, issued by the State Intellectual Property Office of China, with English translation, corresponding Chinese patent application Serial No. 201080010548.4; dated Mar. 22, 2013, 20 pages, P.R. China.

(Continued)

*Primary Examiner* — Mirellys Jagan
(74) *Attorney, Agent, or Firm* — Barbara A. Wrigley; Oppenheimer Wolff & Donnelly LLP

(57) ABSTRACT

A method of estimating temperature includes selecting a plurality of known calibration temperature values; determining a bulk wavelength for each of the calibration temperature values; formulating a calibration data set that includes the plurality of known temperature values and the corresponding plurality of bulk wavelengths; and using the calibration data set to determine an estimated current temperature value based upon a current bulk wavelength, wherein the current temperature value is estimated based upon one or more data points in the calibration data set.

20 Claims, 15 Drawing Sheets

(56) References Cited

U.S. PATENT DOCUMENTS

| | | |
|---|---|---|
| 2007/0156212 A1 | 7/2007 | Saxena et al. |
| 2007/0288058 A1 | 12/2007 | Halperin et al. |
| 2008/0119919 A1 | 5/2008 | Atalar et al. |
| 2008/0243218 A1 | 10/2008 | Bottomley et al. |
| 2009/0137952 A1 | 5/2009 | Ramamurthy et al. |
| 2009/0171421 A1 | 7/2009 | Atalar et al. |
| 2010/0114276 A1 | 5/2010 | Min et al. |
| 2011/0292965 A1* | 12/2011 | Mihailov ............... 374/121 |
| 2012/0179068 A1 | 7/2012 | Leo et al. |
| 2013/0066228 A1 | 3/2013 | Capcelea et al. |
| 2013/0090563 A1 | 4/2013 | Weber |
| 2013/0193961 A1* | 8/2013 | Wen et al. ............ 324/244.1 |

OTHER PUBLICATIONS

International Preliminary Report on Patentability, issued by the International Bureau of WIPO regarding corresponding PCT patent application Serial No. PCT/2010/026225; dated Sep. 6, 2011, 6 pages.

International Search Report, issued by the U.S. Receiving Office (USPTO) regarding corresponding PCT patent application Serial No. PCT/2010/026225; dated Jul. 6, 2010, 3 pages.

* cited by examiner

| CALIBRATION DATA SET | |
|---|---|
| $\lambda$cal 0 | Tcal 0 |
| $\lambda$cal 1 | Tcal 1 |
| $\lambda$cal 2 | Tcal 2 |
| • | • |
| • | • |
| • | • |
| $\lambda$cal n | Tcal n |

METHOD FOR MRI COMPATIBLE MEDICAL DEVICE TEMPERATURE MONITORING

CROSS REFERENCE TO RELATED APPLICATIONS

This application is a continuation of U.S. patent application Ser. No. 13/202,691, filed Aug. 22, 2011, which is a national stage patent application of PCT/US2010/26225, filed Mar. 4, 2010, which is a non-provisional of U.S. Ser. No. 61/157,471, filed Mar. 4, 2009, the entireties of which are incorporated by reference herein.

FIELD OF THE INVENTION

The invention relates to medical devices used in diagnostic and therapeutic procedures and in particular to a system and method for monitoring temperature of a medical device in a magnetic resonance imaging environment.

BACKGROUND OF THE INVENTION

MRI has achieved prominence as a diagnostic imaging modality, and increasingly as an interventional imaging modality. The primary benefits of MRI over other imaging modalities, such as X-ray, include superior soft tissue imaging and avoiding patient exposure to ionizing radiation produced by X-rays. MRI's superior soft tissue imaging capabilities have offered great clinical benefit with respect to diagnostic imaging. Similarly, interventional procedures, which have traditionally used X-ray imaging for guidance, stand to benefit greatly from MRI's soft tissue imaging capabilities. In addition, the significant patient exposure to ionizing radiation associated with traditional X-ray guided interventional procedures is eliminated with MRI guidance.

MRI uses three fields to image patient anatomy: a large static magnetic field, a time-varying magnetic gradient field, and a radiofrequency (RF) electromagnetic field. The static magnetic field and time-varying magnetic gradient field work in concert to establish both proton alignment with the static magnetic field and also spatially dependent proton spin frequencies (resonant frequencies) within the patient. The RF field, applied at the resonance frequencies, disturbs the initial alignment, such that when the protons relax back to their initial alignment, the RF emitted from the relaxation event may be detected and processed to create an image.

Each of the three fields associated with MRI present safety risks to patients when a medical device is in close proximity to or in contact either externally or internally with patient tissue. One important safety risk is the heating that can result from an interaction between the RF field of the MRI scanner and the medical device (RF-induced heating), especially medical devices which have elongated conductive structures with tissue contacting electrodes, such as electrode wires in pacemaker and implantable cardioverter defibrillator (ICD) leads, guidewires, and catheters. Thus, as more patients are fitted with implantable medical devices, and as use of MRI diagnostic imaging continues to be prevalent and grow, the need for safe devices in the MRI environment increases.

A variety of MRI techniques are being developed as an alternative to X-ray imaging for guiding interventional procedures. For example, as a medical device is advanced through the patient's body during an interventional procedure, its progress may be tracked so that the device can be delivered properly to a target site. Once delivered to the target site, the device and patient tissue can be monitored to improve therapy delivery. Thus, tracking the position of medical devices is useful in interventional procedures. Exemplary interventional procedures include, for example, cardiac electrophysiology procedures including diagnostic procedures for diagnosing arrhythmias and ablation procedures such as atrial fibrillation ablation, ventricular tachycardia ablation, atrial flutter ablation, Wolfe Parkinson White Syndrome ablation, AV node ablation, SVT ablations and the like. Tracking the position of medical devices using MRI is also useful in oncological procedures such as breast, liver and prostate tumor ablations; and urological procedures such as uterine fibroid and enlarged prostate ablations.

In many of the foregoing cases, elongated or large surface area metallic structures may be present in interventional devices that are used during a procedure to deliver therapy or provide a diagnosis, implanted devices that are placed within the body to provide therapy or deliver a diagnosis, or the tools used to deploy or deliver the interventional or implanted device to the patient. Examples of interventional devices having metallic structures may include plaque excision devices, embolic traps, electrophysiology catheters, biopsy needles/tools, and stem cell delivery catheters. Examples of implanted devices having metallic structures may include cochlear implants, pacemakers, implantable cardioverter defibrillators, Insulin pumps, nerve stimulators, lead wires, prosthetic heart valves, hemostatic clips, and non-ferromagnetic stapedial implants. Finally, examples of deployment or delivery tools having metallic structures may include catheters, sheaths, introducers, guidewires, transseptal devices, and trochars.

As appreciated by those skilled in the art, these metallic structures may undergo heating during an MRI scanning process. This heating may be caused by numerous factors, including but not limited to eddy currents from MRI gradient switching, RF induced heating due to electromagnetic interactions between the metallic structure and the MRI transmit coil, and large current densities at metal/tissue interfaces (where heating may occur in both the metallic structure as well as the connected tissue). In all of these cases, it may be important to monitor the device temperature at a single or multiple points such that a safe level of device heating may be maintained.

In some of the foregoing cases, the interventional procedure may also include delivery of ablative therapy in the form of either heat, such as by radiofrequency delivery, laser delivery, microwave delivery, or highly focused ultrasound delivery, or freezing, such as by delivery of a cryogenic fluid. When the interventional procedure includes the delivery of ablative energy, it may be especially important to monitor the temperature of the therapy delivery point such that the therapy can be appropriately titrated. Thus, temperature monitoring is an important step for interventional procedures performed under MRI guidance.

Numerous methods and devices for measuring temperature are known and used in the medical device field. One exemplary device for measuring temperature is a thermocouple. Generally speaking, a thermocouple may be any conductor that generates a voltage when subjected to a thermal gradient. Thermocouples typically use two dissimilar metals to create a circuit in which the two legs generate different voltages that may be measured to determine a temperature value. Thermopile devices operate in a similar manner and are constructed by connecting a plurality of thermocouples in series or parallel. Another exemplary device for measuring temperature is a resistance thermometer or resistance temperature detector (RTD). This type of device operates by exploiting the predictable change in electrical resistance of materials with changing temperature, and is typically made of platinum. Yet another exemplary device for measuring temperature is a thermistor. Thermistors utilize a type of resistor that exhibits a varying resistance according to its temperature. Both positive and negative coefficient devices exist (PTC and NTC). As opposed to RTDs which are formed from pure metals, thermistors are generally formed from a ceramic or polymer.

One exemplary method of measuring temperature is known as radiation thermometry. Every object emits radiant energy, and the intensity of this radiation per unit area is a function of its temperature. In radiation thermometry, infrared thermometers are used to measure intensity of radiation. Radiation thermometry is also commonly referred to as optical pyrometry, radiometric temperature measurement, infrared thermometry, optical fiber thermometry, two color radiation thermometry, and infrared thermometry. Another exemplary method of measuring temperature is based upon the semiconductor absorption theory, and may be referred to as the method of "spectral analysis." Spectral analysis uses gallium arsenide (GaAs) tipped fibers, and operates on the absorption/transmission properties of gallium arsenide crystal semiconductors. As the crystal temperature increases, its transmission spectrum shifts to a higher wavelength. The relationship between temperature and the wavelength at which the absorption shift takes place is predictable. The temperature value may be obtained by analyzing the absorption spectrum. Yet another method of measuring temperature is known as fluoroptic thermometry. When thermo-sensitive phosphor is stimulated with red light it emits light over a broad spectrum in the near infrared region. The time required for the fluorescence to decay is dependent upon the sensor's temperature. The measured decay time may be converted to temperature using a calibrated conversion table.

The foregoing known devices and methods for measuring temperature have numerous disadvantages and limitations. Thermocouples are inaccurate, susceptible to MRI-induced heating due to their metallic nature, and require conductive leads that can create a non-MRI safe condition. Resistance thermometers or RTDs require conductive leads that can create a non-MRI safe condition and are mechanically fragile. Thermistors also require conductive leads that can create a non-MRI safe condition and are mechanically fragile. With regard to radiation thermometry, radiation amplitude at body temperatures is small and requires large area detectors. Further, it is difficult to provide sufficient lensing at the tip of the catheter. Spectral analysis is expensive, potentially toxic in the body due to the use of gallium arsenide, and the fibers are difficult to manufacture. Fluoroptic thermometry is also an expensive and inaccurate process that requires calibration before each use. Further, it is difficult to localize the temperature measurement point, and process testing cannot be exposed to ambient light.

Current technologies for measuring temperature in an MRI environment are inadequate. Therefore, what is needed is a real-time temperature measurement system that is MRI safe, accurate, biocompatible, and cost effective.

BRIEF SUMMARY OF THE INVENTION

The present invention solves the foregoing needs by providing a novel MRI compatible temperature measurement system and method for a medical device. In one exemplary embodiment, a temperature monitoring system is provided that includes an optical transmit/receive unit, an elongate optical fiber having a proximal end, a distal end, and an inner core extending between the proximal end and the distal end, and one or more fiber Bragg grating elements formed in the inner core of the optical fiber. The optical fiber is operably coupled to the transmit/receive unit at the proximal end. At least a portion of the optical fiber is also operably coupled to a medical device and is structured to measure temperature at one or more temperature sensing locations on the medical device.

In accordance with another aspect of the present invention, a method of estimating temperature is provided that generally includes the steps of selecting a plurality of known calibration temperature values, determining a bulk wavelength for each of the calibration temperature values, formulating a calibration data set that includes the plurality of known temperature values and the corresponding plurality of bulk wavelengths, and using the calibration data set to determine an estimated current temperature value based upon a current bulk wavelength, wherein the current temperature value is estimated based upon one or more data points in the calibration data set.

DETAILED DESCRIPTION OF THE INVENTION

Figure 1:
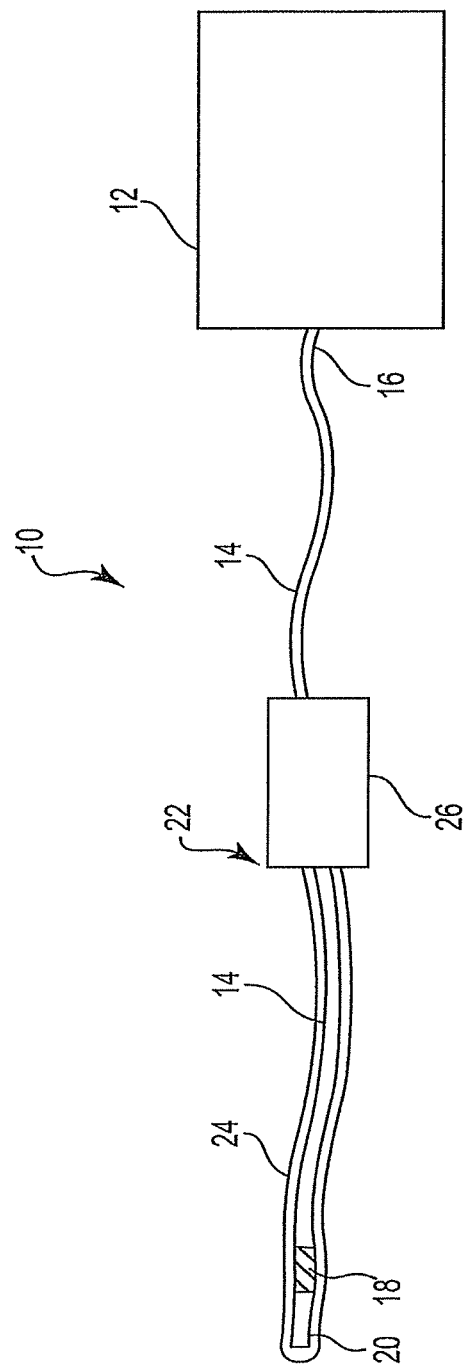
FIG. 1 is a diagram illustrating one exemplary temperature monitoring system in accordance with the present invention.

FIG. 1 is a diagram illustrating one exemplary temperature monitoring system 10 in accordance with the present invention. As illustrated in FIG. 1, the temperature monitoring system 10 generally includes an optical transmit/receive circuitry unit 12 and a fiber 14 operably coupled on a proximal end 16 to the optical transmit/receive circuitry 12. The fiber 14 may preferably be formed from glass or plastic, and further includes a fiber Bragg grating (FBG) element 18 adjacent a distal end 20. In the exemplary embodiment of FIG. 1, the temperature monitoring system 10 is shown as being used with a catheter 22. The catheter 22 includes a main body 24 structured to receive at least a portion of the fiber 14 and a catheter handle 26 structured to be grasped and held by a surgeon or support device. As will be appreciated by those skilled in the art, the catheter 22 is represented generically herein and may be structured for use in numerous types of medical procedures to deliver therapy or provide a diagnosis.

Figure 2:
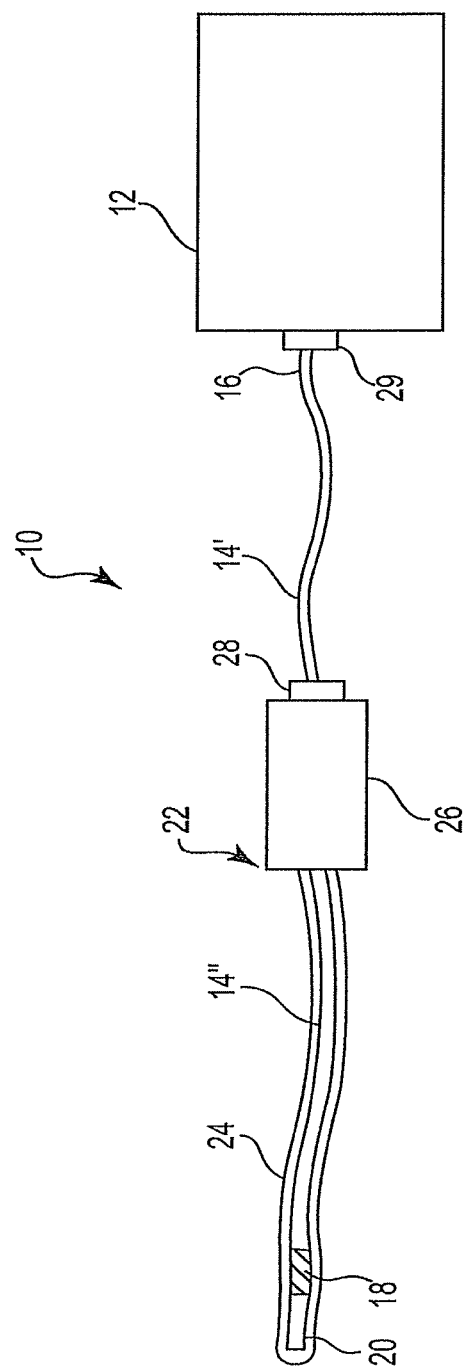
FIG. 2 is a diagram illustrating a modified design for the temperature monitoring system of FIG. 1.

The fiber 14 of the temperature monitoring system 10 may be structured such that it is completely removable from the catheter 22 and may be reused in a different catheter or another type of medical device. Alternatively, as illustrated in FIG. 2, the fiber may comprise a first portion 14' that is fixedly coupled to the optical transmit/receive circuitry 12 and a second portion 14" that is fixedly coupled to the catheter 22. As will be appreciated by those skilled in the art, the first and second portions 14' and 14" may be formed as separate fiber segments. In this alternative fiber design, the catheter handle 26 may include a connector 28 that allows the first portion 14' of the fiber to be optically coupled to the second portion 14" to transmit light waves toward the FBG element 18. Optionally, the optical transmit/receive circuitry 12 may include a connector 29 that allows the first portion 14' to be removably coupled thereto. As will be appreciated by those skilled in the art, connectors 28 and 29 may comprise any suitable connection means without departing from the intended scope of the present invention.

The FBG element 18 positioned or embedded within the main body 24 of the catheter 22 allows a user such as a surgeon to monitor temperature during a medical procedure. As will be appreciated by those skilled in the art, one or more FBGs may be used to monitor temperature during therapy delivery. Alternatively or additionally, one or more FBGs may be used to monitor medical device heating during scanning such that safe levels of heating may be maintained.

Generally speaking, an FBG is one type of distributed Bragg reflector that is constructed in a segment of optical fiber and is structured to reflect predetermined wavelengths of light and to transmit all others therethrough. This selective reflection is accomplished by adding a periodic variation to the refractive index of the optical fiber core, thereby creating a wavelength specific dielectric mirror. Thus, FBGs act as "filters" to block or reflect certain wavelengths.

FBGs are typically formed in an optical fiber by either "writing" or "inscribing" the periodic (or aperiodic) variation of refractive index into the core of the optical fiber using an ultraviolet source. The methods used to create the variations include "interference" and "masking." The interference method, which may be useful for uniform gratings, utilizes an ultraviolet laser that is split into two separate beams that interfere with one another to create a periodic intensity distribution along the interference pattern. The magnitude of the refractive index is dependent upon the intensity of the laser light used. The masking method, which is well-suited for the manufacture of chirped FBGs, utilizes a photomask placed between an ultraviolet light source directed at the fiber and creates a grating structure based upon the intensity of the light that impinges upon the fiber. In another common method, an ultraviolet laser beam may be operated to "write" the grating into the fiber point-by-point.

As appreciated by those skilled in the art, FBGs operate on a principle known as "Fresnel reflection," wherein light traveling between media of different refractive indices may be both reflected and refracted at the interface. The grating of the FBG element includes a varying sinusoidal refractive index over the length of the element. The wavelength reflected by the grating, which is known as the Bragg wavelength, may be approximated as follows:

Bragg wavelength=2.eta..LAMBDA., where .eta. represents the average refractive index in the grating of the fiber and .LAMBDA. represents the grating period.

The refractive index and the grating period are determined by the structure of the FBG element. Generally speaking, there are six known and common structures for FBGs, including chirped, superstructure, Gaussian apodized, discrete phase shift, uniform positive-only index change, and raised-cosine apodized.

Because the Bragg wavelength is sensitive to temperature, FBGs may be used as sensing elements in optical fiber sensors. In a FBG element, the measurand causes a shift in the Bragg wavelength. The relative shift in the Bragg wavelength due to an applied strain (.epsilon.) and a change in temperature (.DELTA.T), may be approximated as follows:

Relative shift in Bragg wavelength=C.sub.S.epsilon.+C.sub.T.DELTA.T, wherein C.sub.S is the coefficient of strain and C.sub.T is the coefficient of temperature.

Based upon the foregoing relationship, FBGs may be used to directly sense the temperature and determine changes in temperature. Various other methods of estimating temperature with FBGs are also possible. A more detailed, exemplary method for estimating temperature using FBGs will be described in further detail to follow.

The fiber 14 of the temperature monitoring system 10 may be either a single-mode or multi-mode fiber optic cable. As appreciated by those skilled in the art, single-mode fiber optical cables are structured for carrying only a single ray or mode of light, which may contain a variety of different wavelengths. Single-mode cables have a small light carrying core, and are well-suited for long distance transmissions. Conversely, multi-mode fiber optic cables have a relatively larger light carrying core, and are well-suited for short distance transmissions.

Although only one FBG element 18 is illustrated in FIG. 1, temperature monitoring systems having any number of FBG elements are within the intended scope of the present invention. In one exemplary embodiment each FBG element may have an axial length (along the axis of the fiber) between about 2 mm and about 6 mm. However, the lengths of the FBGs may be greater than 6 mm or less than 2 mm depending upon the requirements and intended operation of the system. For example, in one alternative embodiment the fiber may include a plurality of FBGs each having a length less than 2 mm in order to optimize spatial selectivity.

The optical transmit/receive circuitry 12 is illustrated as being external to the catheter 14 of FIG. 1 merely for purposes of example and not limitation. In alternative embodiments, the optical transmit/receive circuitry 12 may instead be positioned within or embedded into the medical device in which the temperature is being monitored.

Figure 3:
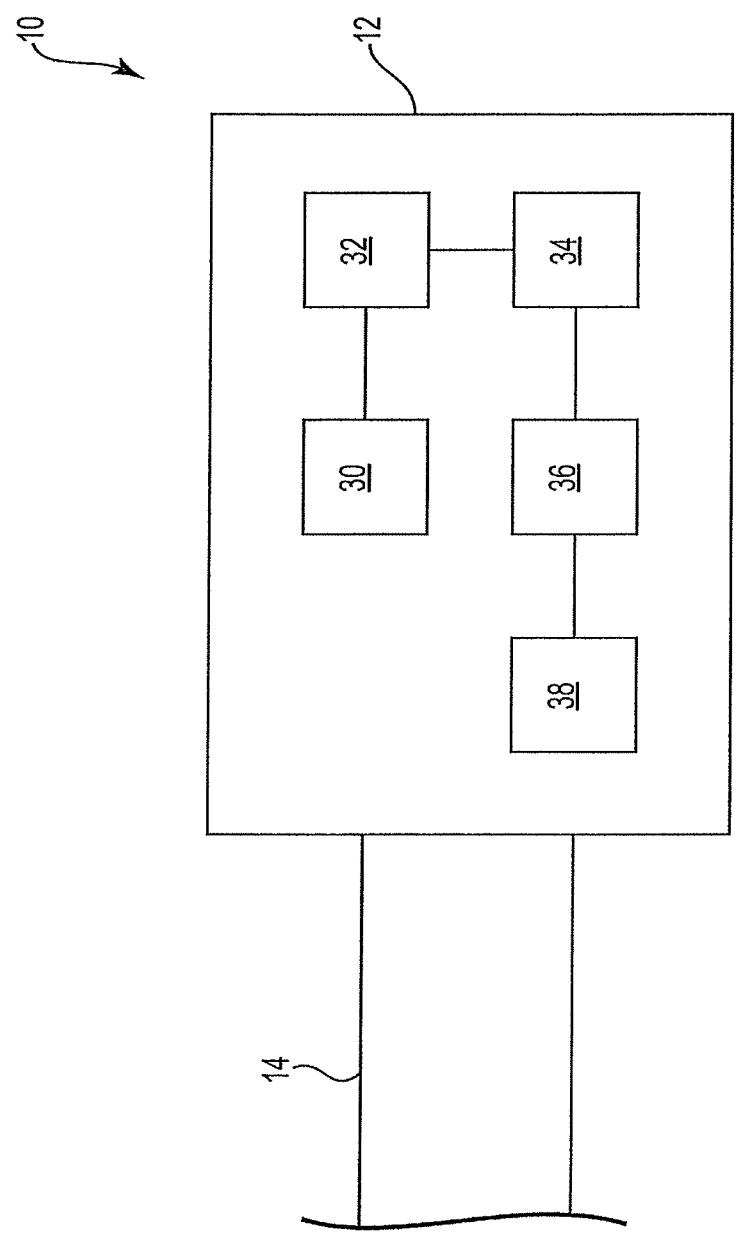
FIG. 3 is a block diagram illustrating the components of an exemplary optical transmit/receive circuitry unit.

FIG. 3 is a block diagram illustrating the components of an exemplary optical transmit/receive circuitry 12. As illustrated in FIG. 3, the optical transmit/receive circuitry 12 includes a light source 30, a tunable filter 32, a scan generator 34, a processor 36, and a detector 38. The light source 30 may be a narrowband or broadband light source (i.e. white light). The tunable filter 32 and the detector 38 are operable to detect wavelength of the received light (i.e. tunable wavelength filter).

In operation, the scan generator 34 may tune the light source 30 by sweeping it across a predetermined range so that the wavelength of light being transmitted down the fiber 14 is known at all times. When the wavelength emitted by the light source 30 matches the specified Bragg wavelength of the FBG element 18, light is reflected back along the fiber 14 towards the detector 38. The scan generator 34 is operable to transmit a timing signal to the processor 36. This timing signal allows the processor to create a "spectrum" based upon the "intensity" versus "time" information it has received. The processor may be operable to identify various characteristics of the spectrum such as peak positions, which may then be used to estimate temperature.

Figure 4:
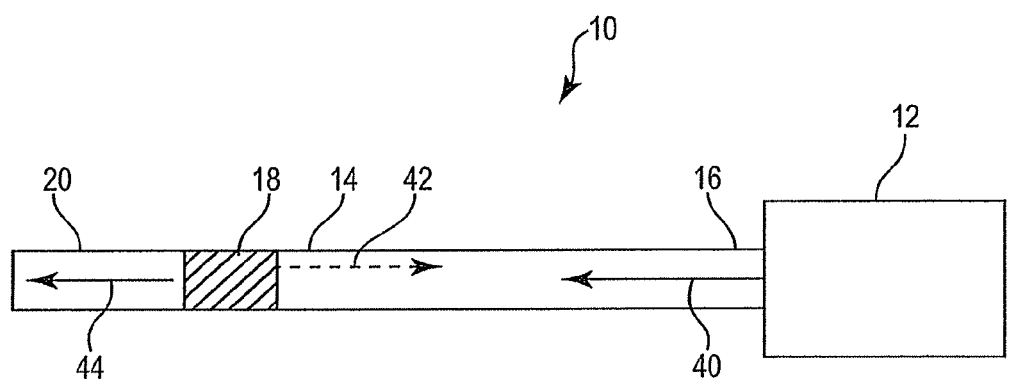
FIG. 4 is a block diagram illustrating the basic operation of the temperature monitoring system of FIG. 1.

FIG. 4 is a block diagram illustrating the basic operation of the temperature monitoring system 10 in accordance with the present invention. As shown in FIG. 4, light waves 40 (either narrowband or broadband) are transmitted from the optical transmit/receive circuitry 12 towards the FBG element 18. The FBG element 18 reflects a predetermined narrow or broad range of wavelengths of light 42 incident on the grating while passing all other wavelengths of light 44. The reflected wavelengths 42 are redirected back towards the optical transmit/receive circuitry 12 where they are detected by the tunable filter 32 and the detector 38 as previously described above with regard to the system block diagram of FIG. 3.

Figure 5:
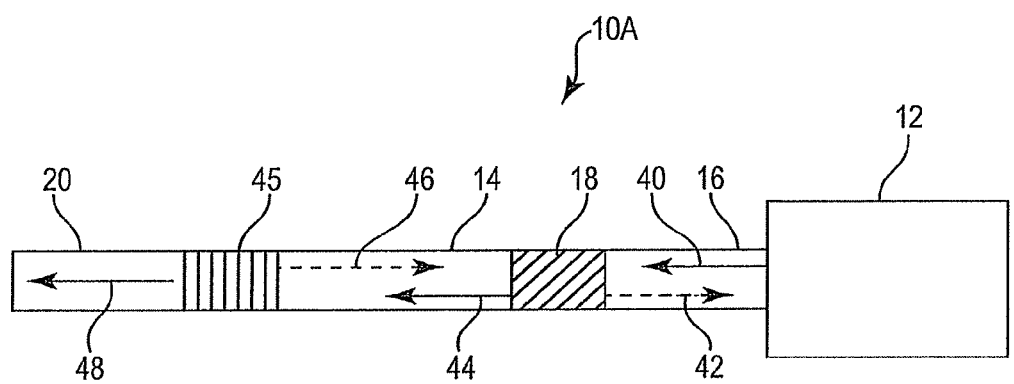
FIG. 5 is a block diagram illustrating the basic operation of an alternative temperature monitoring system in accordance with the present invention.

FIG. 5 is a block diagram illustrating the basic operation of an alternative temperature monitoring system 10A in accordance with the present invention. The temperature monitoring system 10A is similar to the temperature monitoring system 10 previously described, but further includes a second FBG element 45 positioned along the fiber 14. Because wavelengths other than the Bragg wavelength are passed with little or no attenuation, multiple FBGs may be used on a single fiber. As shown in FIG. 5, light waves 40 (either narrowband or broadband) are transmitted from the optical transmit/receive circuitry 12 towards the FBG element 18. The FBG element 18 reflects a predetermined narrow or broad range of wavelengths of light 42 incident on the grating while passing all other wavelengths of light 44. The reflected wavelengths 42 are redirected back towards the optical transmit/receive circuitry 12 where they are detected by the tunable filter 32 and the detector 38 as previously described above with regard to the system block diagram of FIG. 3. The wavelengths of light 44 that are allowed to pass through the FBG element 18 are directed towards the second FBG element 45, where a second predetermined narrow or broad range of wavelengths of light 46 are reflected back towards the optical/transmit receive circuitry 12 where they are also detected by the tunable filter 32 and the detector 38. All other wavelengths of light 48 are passed through the second FBG element 45 towards the distal end 20 of the fiber 14. As will be appreciated by those skilled in the art, the FBG element 18 and the second FBG element 45 must have their own wavelength segments to ensure that various signals do not overlap and the temperature monitoring system operates properly.

Figure 6:
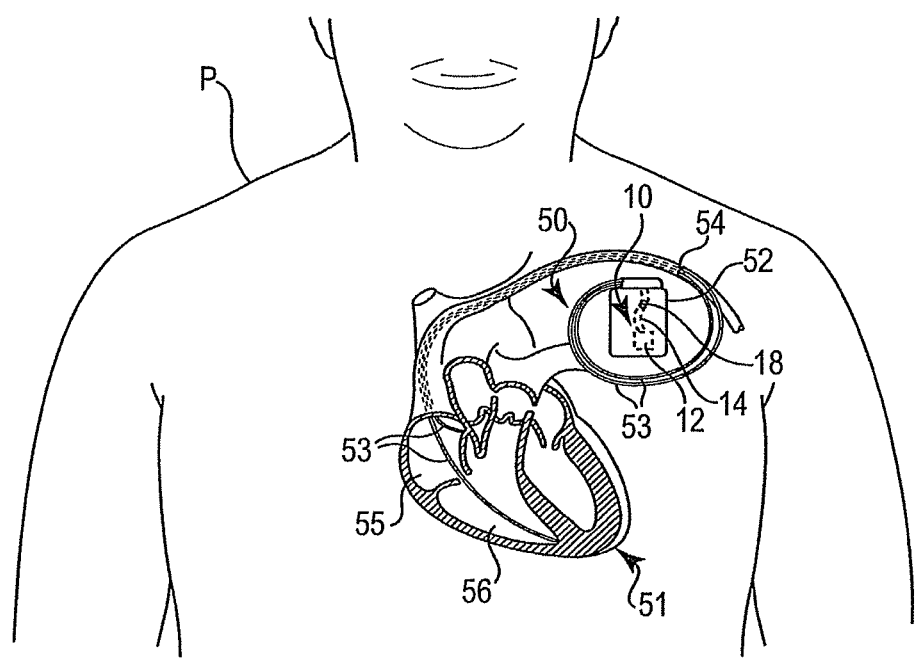
FIG. 6 is an exemplary embodiment of an implantable device having the temperature monitoring system of FIG. 1 embedded therein.

FIG. 6 is an exemplary embodiment of an implantable device 50 such as a defibrillator having the temperature monitoring system 10 of FIG. 1 embedded therein. As illustrated in FIG. 6, the implantable device 50 may be inserted under the skin of a patient P adjacent the heart 51, and may generally include a main housing 52 along with one or more elongate electrodes 53 insertable through a vein 54 and sized to extend into the right atrium 55 and the right ventricle 56. As will be appreciated by those skilled in the art, the size and structure of the implantable device 50 may vary without departing from the intended scope of the present invention.

As further illustrated in FIG. 6, both the fiber 14 and the optical transmit/receive circuitry 12 are positioned or embedded within the housing 52 such that the temperature monitoring system 10 is completely contained within the implantable device 50. In operation, the temperature monitoring system 10 is operable to sense temperature adjacent to the implantation position of the housing 52. Although a single FBG element that produces a corresponding single temperature sensing location is shown, those skilled in the art will appreciate that any number of FBG elements may be used to achieve any desired number of temperature sensing locations within the housing 52 or along the axial length of the electrodes 53 without departing from the intended scope of the present invention.

Figure 7:
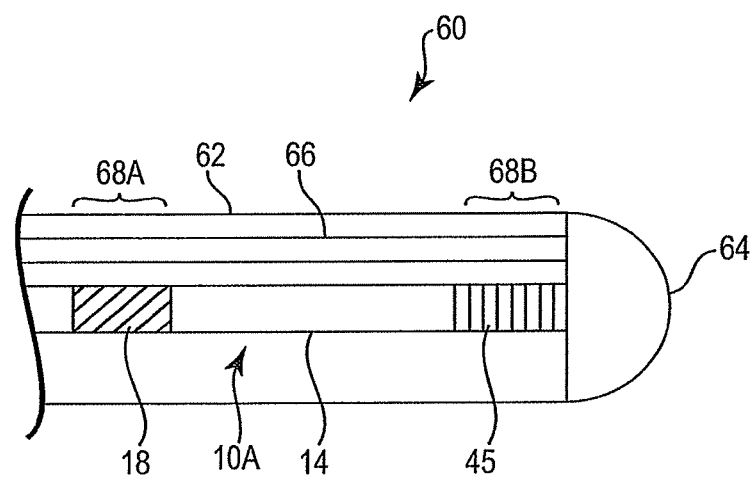
FIG. 7 is an exemplary embodiment of an ablation catheter having the temperature monitoring system of FIG. 5 embedded therein.

FIG. 7 is an exemplary embodiment of an ablation catheter 60 having the temperature monitoring system 10A of FIG. 5 embedded therein. As illustrated in FIG. 7, the ablation catheter 60 includes a generally tubular main body 62, an ablation tip 64, and a lumen 66 extending along the axial length of the main body 62 towards the ablation tip 64. As will be appreciated by those skilled in the art, the ablation catheter 60 may be structured to deliver any suitable ablative therapy to the ablation tip 64 through the lumen 66 including, but not limited to, radiofrequency energy, laser energy, microwave energy, highly focused ultrasound energy, cryogenic fluid and the like.

As further illustrated in FIG. 7, the embedded fiber 14 of the temperature monitoring system 10A may be operable to sense temperature at a first sensing location 68A adjacent to the FBG element 18 and at a second sensing location 68B adjacent to the FBG element 45. Although the ablation catheter 60 is shown as including two temperature sensing locations 68A and 68B, any number of temperature sensing locations may be created by simply varying the number of FBG elements in the fiber. Additionally, the axial positions of the temperature sensing locations may be altered by modifying the spacing between the FBG elements.

Figure 8:
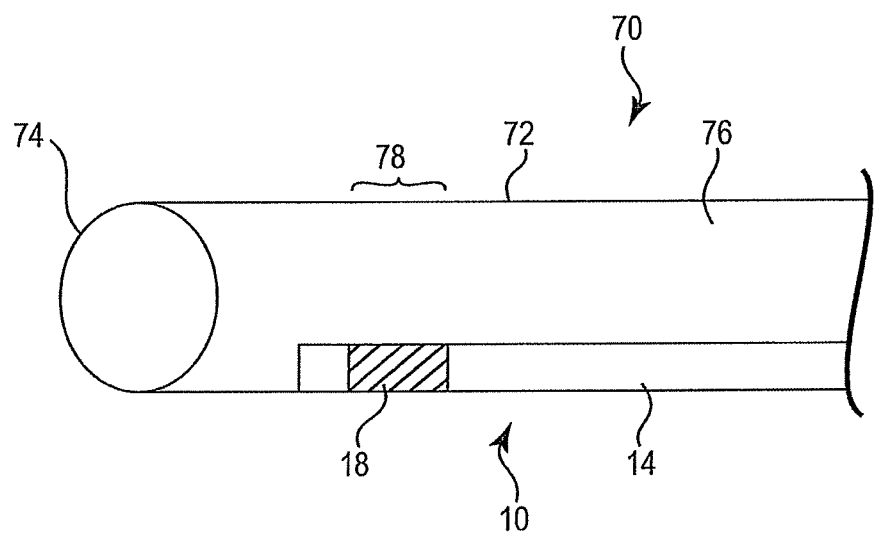
FIG. 8 is an exemplary embodiment of a biopsy needle device having the temperature monitoring system of FIG. 1 embedded therein.

FIG. 8 is an exemplary embodiment of a biopsy needle device 70 having the temperature monitoring system 10 of FIG. 1 embedded therein. As illustrated in FIG. 8, the biopsy needle device 70 includes a generally tubular main body 72, an open distal tip 74, and a lumen 76 extending along the axial length of the main body 72. As will be appreciated by those skilled in the art, the size and structure of the biopsy needle device 70 may vary without departing from the intended scope of the present invention.

As further illustrated in FIG. 8, the embedded fiber 14 of the temperature monitoring system 10 may be operable to sense temperature at a single sensing location 78 adjacent to the FBG element 18. However, as will be appreciated by those skilled in the art, any number of FBG elements may be used to achieve any desired number of temperature sensing locations along the axial length of the biopsy needle device 70.

Additionally, although the FBG element 18 of the fiber 14 is positioned such that it produces a temperature sensing location 78 adjacent to the distal end of the main body 72, the temperature sensing location may be modified by placing the FBG element at another axial location.

Figure 9:
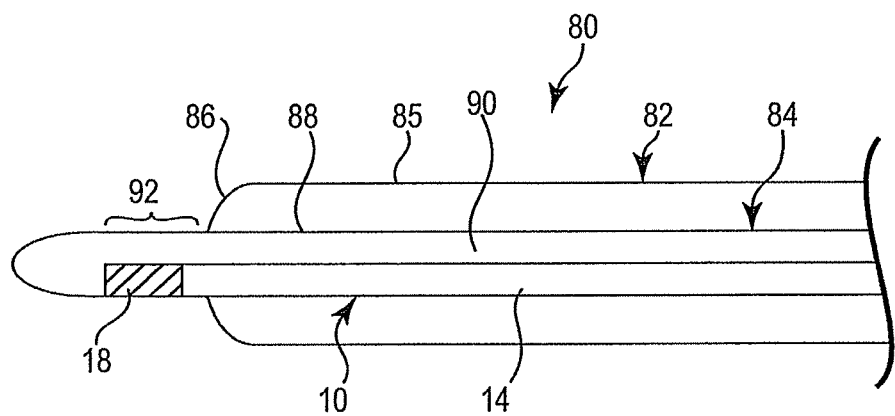
FIG. 9 is an exemplary embodiment of a stem cell delivery device having the temperature monitoring system of FIG. 1 embedded therein.

FIG. 9 is an exemplary embodiment of a stem cell delivery device 80 having the temperature monitoring system 10 of FIG. 1 embedded therein. As illustrated in FIG. 8, the stem cell delivery device 80 includes a catheter 82 and a stem cell delivery needle 84. The catheter 82 includes a generally tubular main body 85 with an open distal end 86 structured to allow the stem cell delivery needle 84 to pass therethrough. The stem cell delivery needle 84 includes an elongate main body 88 have a lumen 90 therein. The fiber 14 with the FBG element 18 is embedded within the lumen 90 of the main body 88 of the stem cell delivery needle 84. The main body 88 may include an aperture at a distal end that is structured and sized for passing cell structures therethrough. As will be appreciated by those skilled in the art, the size and structure of the stem cell delivery device 80 may vary without departing from the intended scope of the present invention.

As further illustrated in FIG. 9, the embedded fiber 14 of the temperature monitoring system 10 may be operable to sense temperature at a single sensing location 92 adjacent to the FBG element 18. As will be appreciated by those skilled in the art, a surgeon may move the stem cell delivery needle 84 relative to the open distal end 86 of the catheter 84 in order to position the temperature sensing location at the desired point (or as close as possible to the desired point) where the surgeon wants to obtain a temperature reading. Similar to the medical devices previously described above, any number of FBG elements may be used to achieve any desired number of temperature sensing locations along the axial length of the stem cell delivery device 80. Additionally, although the FBG element 18 of the fiber 14 is positioned such that it produces a temperature sensing location 92 adjacent to the distal end of the main body 88 of the stem cell delivery needle 84, the temperature sensing location may be modified by placing the FBG element at another axial location.

Figure 10:
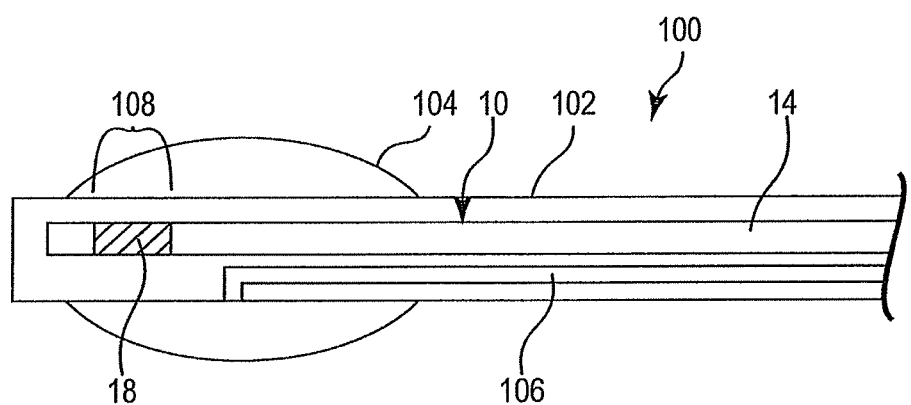
FIG. 10 is an exemplary embodiment of an interventional device delivery system having the temperature monitoring system of FIG. 1 embedded therein.

FIG. 10 is an exemplary embodiment of an interventional device delivery system 100 having the temperature monitoring system 10 of FIG. 1 embedded therein. As illustrated in FIG. 10, the delivery system 100 includes a generally tubular catheter body 102, an expansion means 104 such as a balloon adjacent a distal end, and a lumen 106 extending along the axial length of the catheter body 102. In one exemplary embodiment, the lumen 106 may be structured for passage of an inflation means such as air or saline for inflation and deflation of the expansion means 104. The delivery system 100 may be structured for delivery of any suitable interventional device such as an expandable stent or the like.

As further illustrated in FIG. 10, the embedded fiber 14 of the temperature monitoring system 10 may be operable to sense temperature at a single sensing location 108 adjacent to the FBG element 18. However, as will be appreciated by those skilled in the art, any number of FBG elements may be used to achieve any desired number of temperature sensing locations along the axial length of the interventional device delivery system 100. Additionally, although the FBG element 18 of the fiber 14 is positioned such that it produces a temperature sensing location 108 adjacent to the distal end of the catheter body 102, the temperature sensing location may be modified by placing the FBG element at another axial location.

Figure 11:
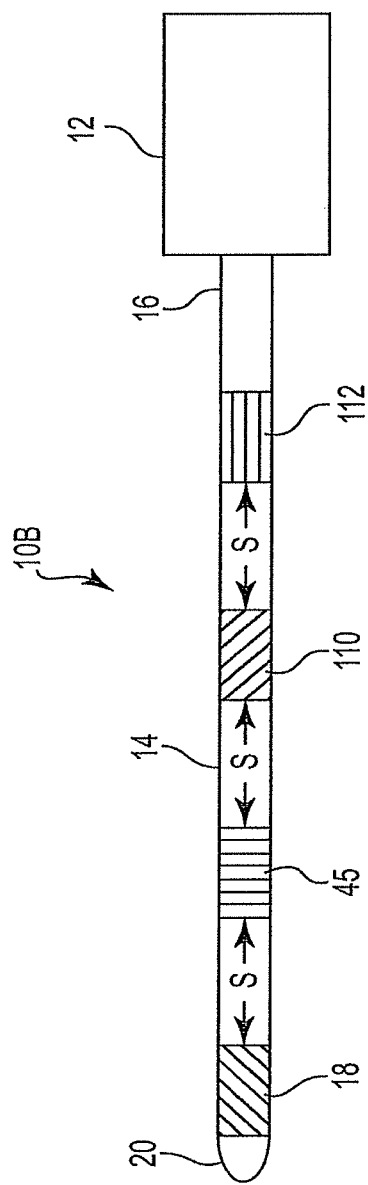
FIG. 11 is an exemplary embodiment of another alternative temperature monitoring system in accordance with the present invention.

FIG. 11 is an exemplary embodiment of another alternative temperature monitoring system 10B in accordance with the present invention. As illustrated in FIG. 11, the temperature monitoring system 10B is similar to the temperature monitoring system 10A, but further includes a third FBG element 110 and a fourth FBG element 112. As will be appreciated by those skilled in the art based on the foregoing discussion, having multiple FBG elements positioned along an axial length of the fiber 14 between the proximal end 16 and the distal end 20 allows for multiple point temperature measurements along a pathway in a medical device. This type of "pathway" temperature monitoring may be useful in any medical device where it may be important to monitor temperature at more than one location, including but not limited to the devices previously described. As illustrated in FIG. 11, the spacing S between the various FBG elements may be equal or alternatively may vary by any desired amount. Thus, the temperature monitoring device 10B may be customized for particular applications and uses.

Although the various embodiments of medical devices were described above as including a single fiber element, temperature monitoring systems utilizing multiple fiber elements each having one or more FBG elements therein are also possible. Thus, a single medical device such as an ablation catheter may be structured with two or more fibers positioned or embedded therein. This type of design may be used for measuring the temperature of one or more therapy delivery points or one or more locations for safety monitoring during therapy delivery or delivery of a medical device using MRI guidance. Further, although the fiber and FBG elements of the temperature monitoring systems have been generally described as embedded or removably positioned within the medical devices, they may alternatively be fixedly or removably coupled to an outer surface of the device without departing from the intended scope of the present invention.

As will be appreciated by those skilled in the art, the optical fiber may be positioned or embedded within a device, positioned on an outer surface of a device, or any combination thereof without departing from the intended scope of the present invention. For example, in one exemplary embodiment the fiber may be partially exposed to the exterior of the device. In another exemplary embodiment the device may include a fiber with at least one portion completely positioned/embedded within the device and at least one additional portion positioned on the exterior of the device. Thus, numerous alternative designs are contemplated and within the intended scope of the present invention.

As a Bragg diffraction grating system does not posses the technical shortcomings of other temperature measuring techniques inside an MRI system, another alternative embodiment of the present invention may include external in vitro or in vivo temperature measurement of a medical device. In this embodiment, a fiber optic cable having one or more FBG elements is placed external to the medical device. As will be appreciated by those skilled in the art, this embodiment may be useful in determining the safety of a medical device in MRI with regard to joule heating at tissue/electrode interfaces, dielectric heating along the length of a metallic structure, gradient induced heating and the like.

Although the temperature monitoring system of the present invention has been described with reference to a discrete number of medical devices, those skilled in the art will appreciate that the temperature monitoring system may be incorporated into any medical device that is used in an MRI environment. Thus, the embodiments set forth herein have been described merely for purposes of example and not limitation.

Now that several exemplary embodiments of the temperature monitoring system have been described with reference to various medical devices, one exemplary method of operating the temperature monitoring systems to determine temperature measurements will be described in detail. The exemplary method of the present invention may generally be separated into three processes, including determining bulk wavelength 200, calibrating temperature 300, and measuring temperature 400. Each of these processes will now be described with reference to FIGS. 12-19.

Figure 12:
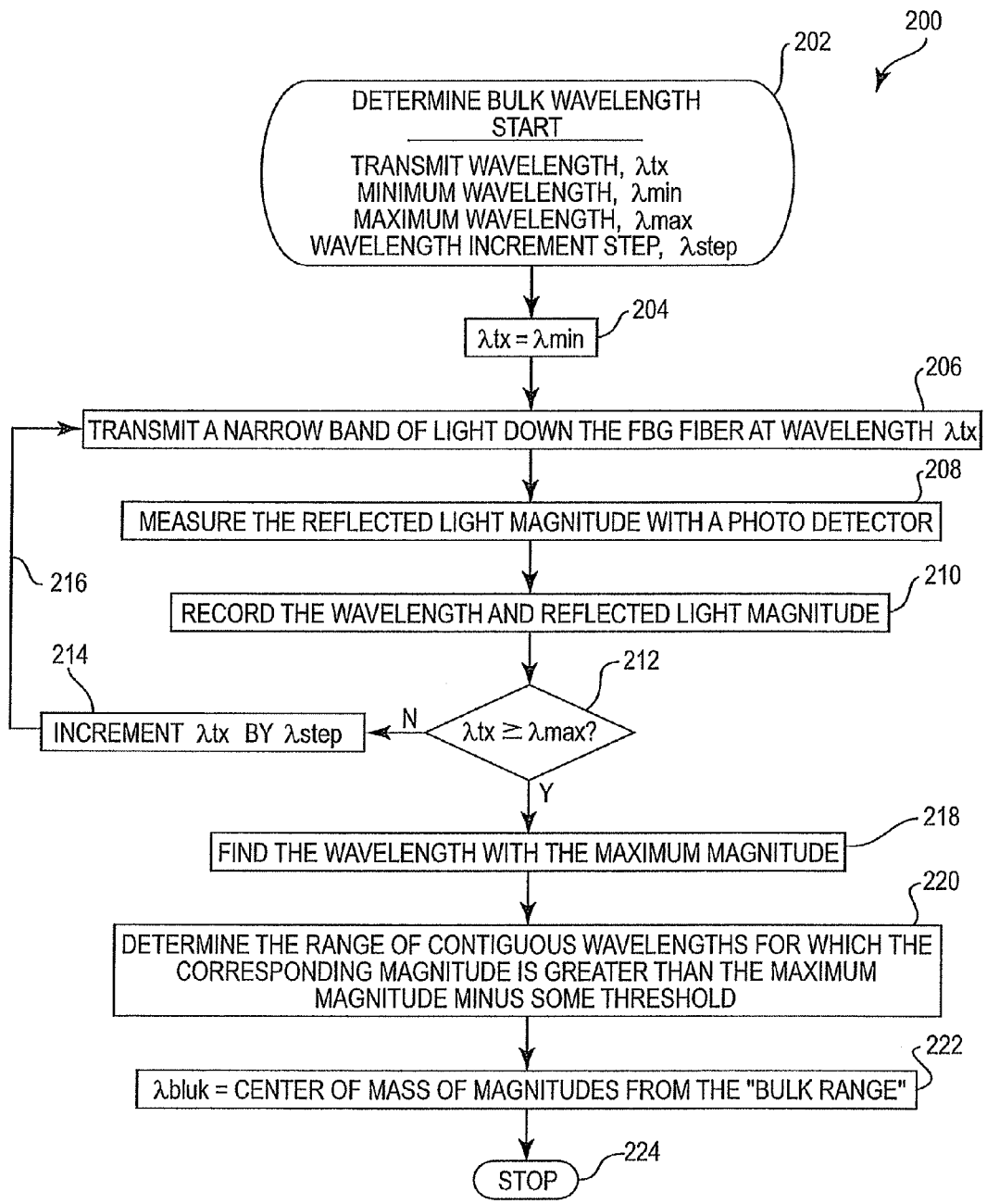
FIG. 12 is a flow diagram illustrating exemplary steps in a process for determining bulk wavelength in accordance with one embodiment of the present invention.

FIG. 12 is a flow diagram illustrating exemplary steps in the process of determining bulk wavelength 200 in accordance with one embodiment of the present invention. Beginning with step 202, three wavelength values are predefined. These wavelength values include the minimum wavelength, .lamda.min, the maximum wavelength, .lamda.max, and the wavelength step, .lamda.step. Then, at step 204 the transmit wavelength, .lamda.tx, is set to the minimum wavelength, .lamda.min.

Starting at the minimum wavelength, the optical transmit/receive unit transmits narrowband (or broadband) light into the proximal end of a fiber containing one or more FBG elements at step 206. The light reflected off of the one or more FBG elements is received and measured by a photo detector in the optical transmit/receive unit at step 208, and the magnitude and transmit wavelength, .lamda.tx, are recorded into memory at step 210.

A processor then determines whether the transmit wavelength, .lamda.tx, is greater than or equal to the maximum wavelength, .lamda.max, at step 212. If the transmit wavelength, .lamda.tx, is determined to be less than the maximum wavelength, .lamda.max, the transmit wavelength, .lamda.tx, is incremented by the wavelength step, .lamda.step, at step 214 and the process 200 enters a loop 216 where steps 206-212 are repeated for transmit wavelengths from .lamda.min to .lamda.max at incremental steps of .lamda.step. Once the processor determines that the transmit wavelength, .lamda.tx, is greater than or equal to the maximum wavelength, .lamda.max, at step 212, this portion of the process is complete and a data set now exists consisting of transmit wavelengths and associated received light magnitudes. An exemplary data set is represented by the graph in FIG. 13.

Figure 13:
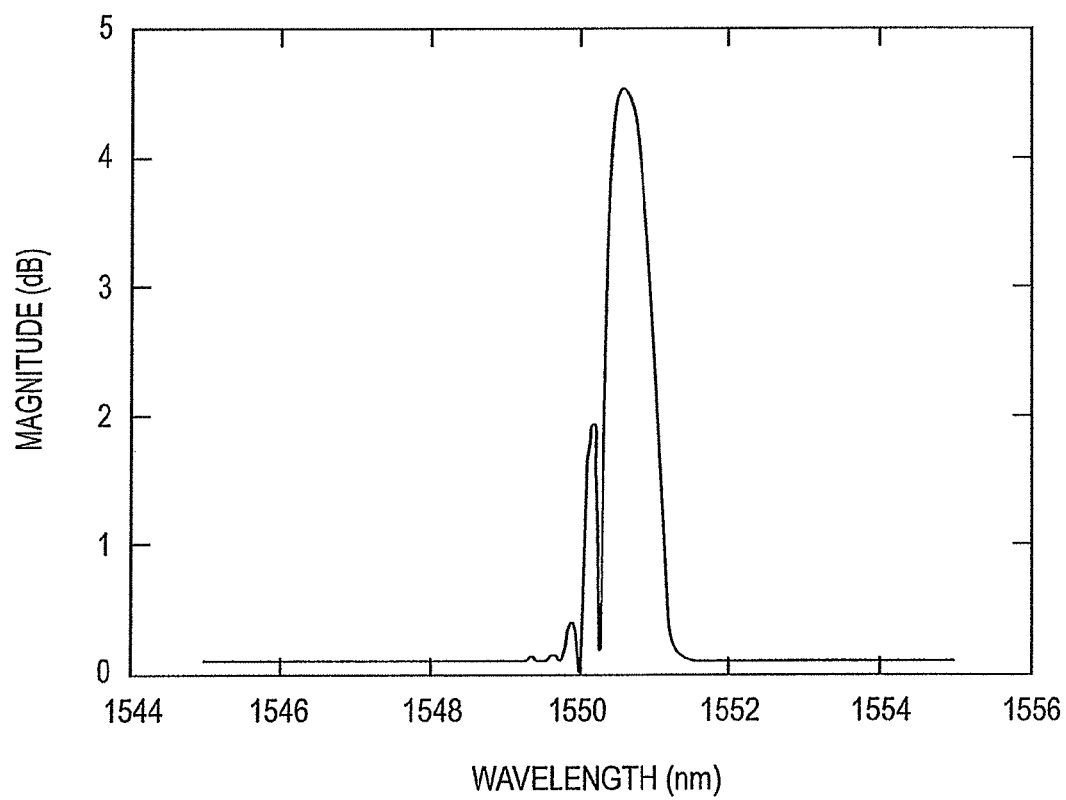
FIG. 13 is a graphical illustration showing an exemplary data set consisting of transmit wavelengths and associated received light magnitudes.
Figure 14:
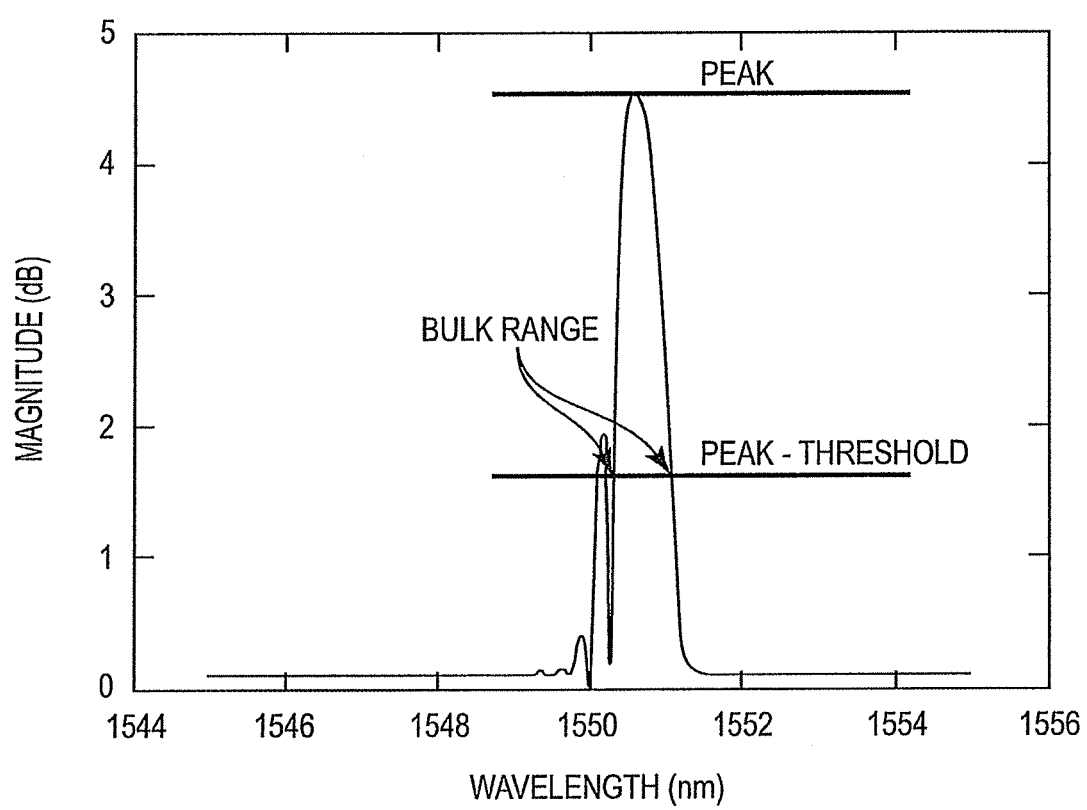
FIG. 14 is a graphical illustration depicting an exemplary bulk range on the data set of FIG. 13.

Although one exemplary method of forming the data set represented by the graph in FIG. 13 has been described in detail, those skilled in the art will appreciate that any suitable method may be used without departing from the intended scope of the present invention. One alternative method is to transmit a broad spectrum of light down the fiber and measure return light intensity variations as the path difference in an interferometer is varied. Another alternative method is to transmit a broad spectrum of light down the fiber and utilize a second fiber Bragg grating element with a known pass/reject ratio through which the returned light is passed, wherein the intensities of the light transmitted through the second fiber Bragg grating element and the light rejected by the second fiber Bragg grating element may be compared to determine the wavelength of the returning light. Yet another alternative method is to transmit a broad spectrum of light down the fiber and split the returned light into several beams which may be fed into many narrowband detectors, each narrowband detector being designed to detect light at a specific wavelength. Yet another alternative method is to transmit multiple narrowband light signals down the fiber, each signal being centered at a different wavelength and each uniquely modulated or coded such that the returned signal can be demodulated or decoded to determine the corresponding intensity vs. wavelength characteristics. As will be appreciated by those skilled in the art, the foregoing alternative methods are presented merely for purposes of example and not limitation.

For purposes of discussion and not limitation, the bulk wavelength may be defined as a single wavelength value that represents the center wavelength of the received light. To find the bulk wavelength, the wavelength at which the magnitude is maximum is first identified at step 218. This step is depicted graphically in FIG. 14. Next, in step 220, the range of contiguous wavelengths (which includes the wavelength at which the magnitude is maximum) for which the corresponding magnitude is greater than the maximum magnitude minus some threshold is determined. This range may be referred to as the "bulk range." In one exemplary embodiment the preferred threshold may be about 3 dB, although any suitable threshold may be used as will be appreciated by those skilled in the art. The bulk wavelength is then calculated in step 222 as the center of mass of the magnitudes within the defined bulk range. This step is also depicted graphically in FIG. 14. As illustrated in the exemplary graph of FIG. 14, the bulk range does not include the small magnitude peak to the left of the main peak. Once the bulk wavelength is calculated at step 222, the process 200 may terminate at step 224.

As will be appreciated by those skilled in the art, bulk wavelength may be calculated using numerous alternative methods without departing from the intended scope of the present invention. For example, bulk wavelength may be determined using peak detection (i.e. finding the absolute peak magnitude value), filtered peak detection (i.e. filtering the wavelength magnitudes followed by finding the absolute peak magnitude value), filtered center of mass (i.e. filtering the wavelength magnitudes followed by finding the center of mass of the magnitudes), or the like. Thus, the bulk wavelength process 200 is one of many processes that may be used, and was discussed herein for purposes of example and not limitation.

Figure 15:
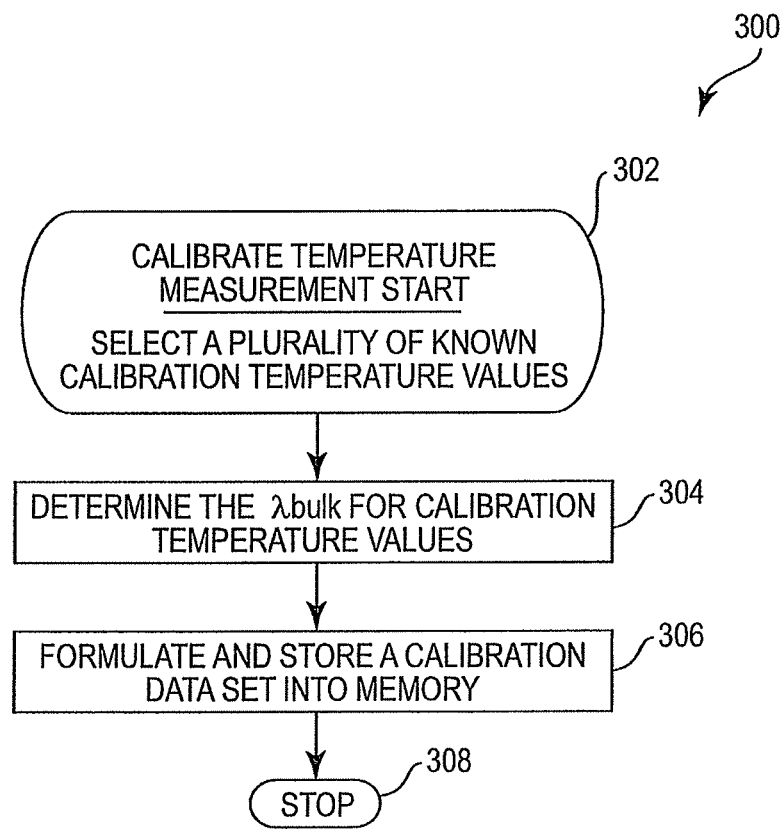
FIG. 15 is a flow diagram illustrating exemplary steps in a temperature calibration process in accordance with one embodiment of the present invention.
Figures 16, 17:
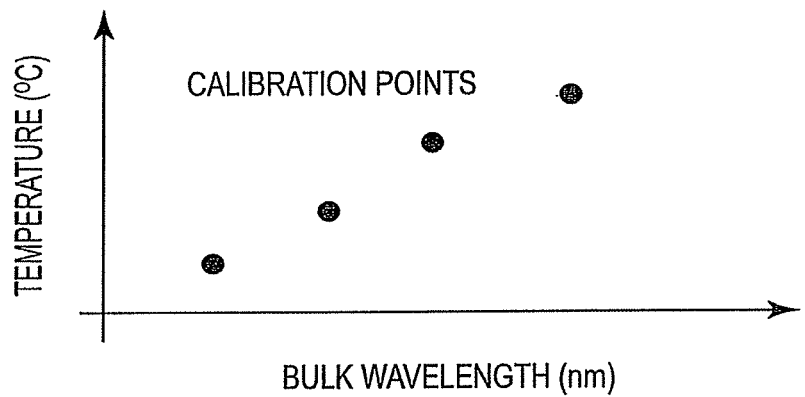
FIG. 16 is a graphical illustration depicting a calibration data set collected during a temperature calibration process.
FIG. 17 is an exemplary calibration data set in table form.

Turning next to FIG. 15, a flow diagram is presented illustrating exemplary steps in the process of calibrating temperature 300 in accordance with one embodiment of the present invention. Beginning with step 302, a plurality of known calibration temperature values are selected that will be used to perform the calibration procedure. Then, in step 304, a bulk wavelength, .lamda.bulk, is determined for each of the selected calibration temperature values. The result of the bulk wavelength determination step is depicted graphically in FIG. 16. These bulk wavelengths may be determined using the bulk wavelength process 200 previously described, or any other known and suitable process for determining bulk wavelength. Once a bulk wavelength is determined for each of the selected calibration temperature values in step 304, a calibration data set is formulated and stored in memory in step 306. In one exemplary embodiment as depicted in the table set forth in FIG. 17, the calibration data set may be stored as a plurality of calibration wavelengths, .lamda.cal, and a corresponding plurality of calibration temperatures, Tcal. Once the calibration data set is stored in memory, the calibration process may terminate at step 308. The stored calibration data set may then be used in the temperature monitoring process 400 to determine the temperature at one or more temperature sensing locations.

Figure 18:
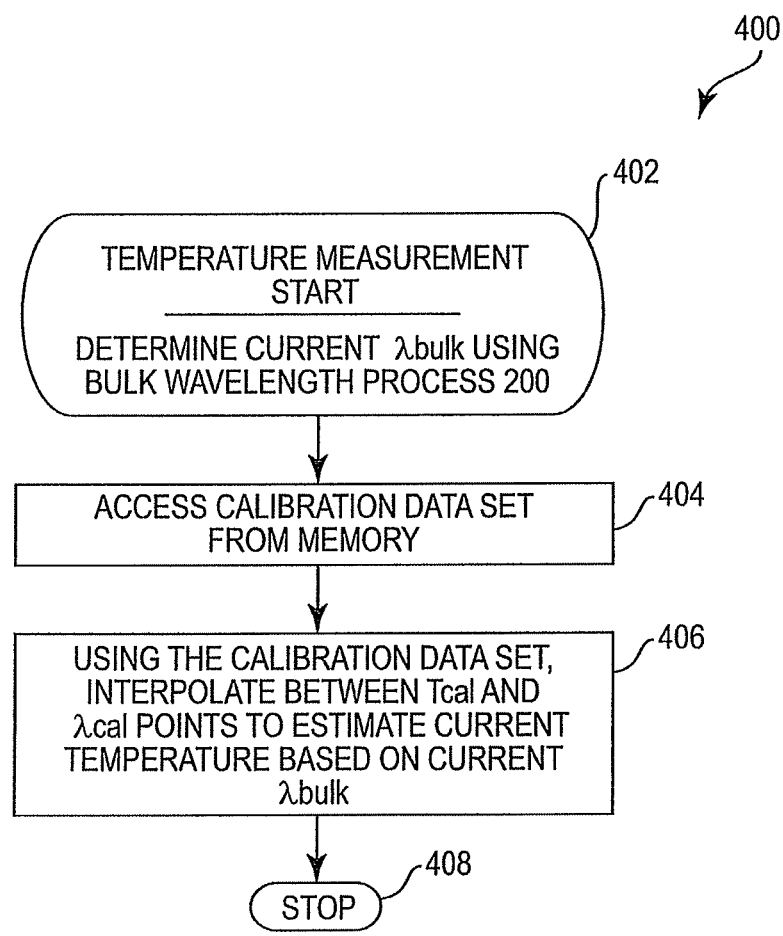
FIG. 18 is a flow diagram illustrating exemplary steps in a temperature measuring process in accordance with one embodiment of the present invention.
Figure 19:
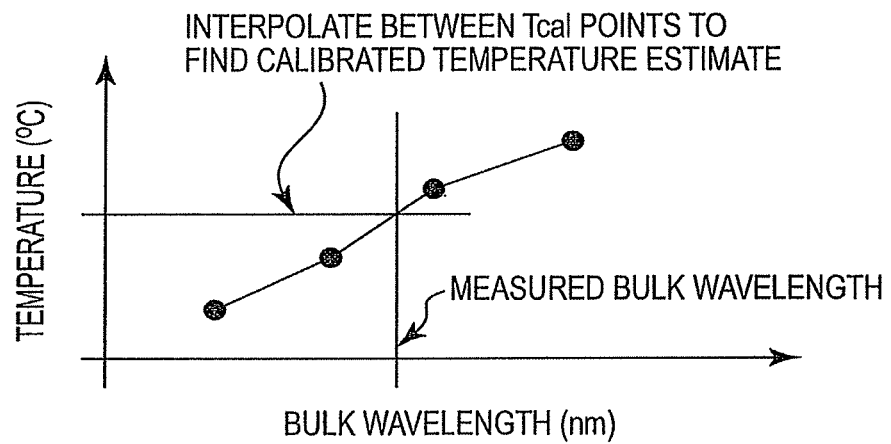
FIG. 19 is a graphical illustration depicting a step for determining an estimated temperature value using interpolation.
Figure 20:
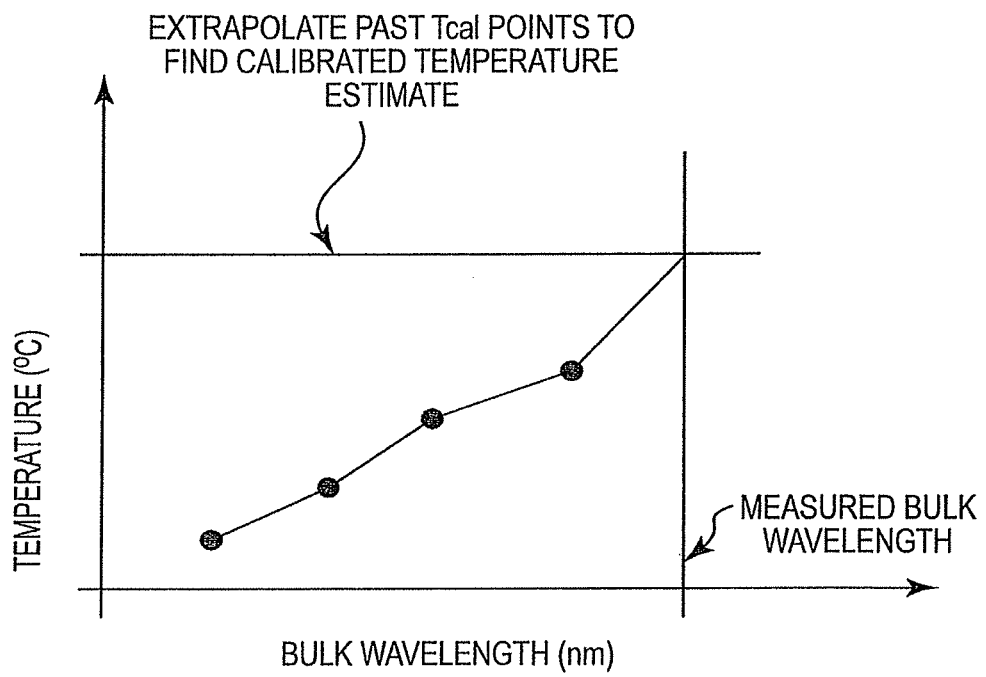
FIG. 20 is a graphical illustration depicting a step for determining an estimated temperature value using extrapolation.

Turning next to FIG. 18, a flow diagram is presented illustrating exemplary steps in the process of measuring temperature 400 at one or more temperature sensing locations in accordance with one embodiment of the present invention. Beginning with step 402, the current bulk wavelength, .lamda.bulk, is determined using any suitable bulk wavelength determination process, such as the bulk wavelength process 200 previously discussed. Next, the calibration data set is accessed from memory in step 404. Using the calibration data set, an interpolation is performed between the appropriate Tcal and .lamda.cal points at step 406 to estimate the current temperature based on the current bulk wavelength. This interpolation process is depicted graphically in FIG. 19. The interpolation step may use linear interpolation or any suitable higher order interpolation, such as polynomial interpolation. If the current bulk wavelength, .lamda.bulk, falls outside of the range of Teal and .lamda.cal points in the calibration data set, step 406 may alternatively utilize extrapolation to estimate the current temperature. This extrapolation process is depicted graphically in FIG. 20. As will be appreciated by those skilled in the art, the extrapolation step may use linear extrapolation or any suitable higher order extrapolation, such as polynomial extrapolation. Once the current temperature is determined in step 406, the temperature monitoring process may terminate at step 408. As will be appreciated by those skilled in the art, the temperature monitoring process 400 may be repeated at any desired time interval in order to continuously or periodically monitor, with or without temporal interpolation or extrapolation, temperature of a device.

Although several exemplary steps were described with reference to the bulk wave determination, temperature calibration, and temperature measurement processes, those skilled in the art will appreciate that the order and number of steps may be modified without departing from the intended scope of the present invention. Thus, the exemplary steps were provided merely for purposes of example and not limitation.

As will further be appreciated by those skilled in the art, the processes previously described may be embodied as a system, method or computer program product. Accordingly, the present invention may take the form of an entirely hardware embodiment, an entirely software embodiment (including firmware, resident software, micro-code, etc.) or an embodiment combining software and hardware aspects that may all generally be referred to as a "circuit," "module" or "system." Furthermore, the present invention may take the form of a computer program product embodied in any tangible medium of expression having computer usable program code embodied in the medium.

The processes comprising the method of the present invention have been described with reference to flow diagrams illustrating exemplary steps. It will be understood that each block of the flowchart diagrams, and combinations of blocks in the flowchart diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart diagram block or blocks.

Although the present invention has been described with reference to preferred embodiments, workers skilled in the art will recognize that changes may be made in and detail without departing from the spirit and scope of the invention.

The invention claimed is:

1. A method of estimating temperature comprising: selecting a plurality of known calibration temperature values; determining a bulk wavelength for each of the calibration temperature values; formulating a calibration data set of data points that includes the plurality of known temperature values and the corresponding plurality of bulk wavelengths; and using the calibration data set to determine an estimated current temperature value based upon a current bulk wavelength, wherein the current temperature value is estimated based upon one or more of the data points in the calibration data set.

2. The method of claim 1, wherein the bulk wavelengths are determined by transmitting a light wave into the proximal end of an optical fiber toward a fiber Bragg grating element and measuring a reflected wavelength magnitude.

3. The method of claim 1, wherein the step of using the calibration data set to determine an estimated current temperature value based upon a current bulk wavelength is repeated at a predefined time interval to periodically monitor temperature of a device.

4. The method of claim 1, further comprising the step of providing a temperature monitoring system comprising: an optical transmit/receive unit; an elongate optical fiber operably coupled to the transmit/receive unit at a proximal end; and a fiber Bragg grating element formed in an inner core of the optical fiber.

5. The method of claim 4, wherein at least a portion of the optical fiber is operably coupled to a medical device and is structured to measure temperature at a temperature sensing location on the medical device.

6. The method of claim 1, wherein the current temperature value is estimated by interpolating between two or more data points in the calibration data set.

7. The method of claim 6, wherein the current temperature value is estimated using linear interpolation.

8. The method of claim 6, wherein the current temperature value is estimated using polynomial interpolation.

9. The method of claim 1, wherein the current temperature value is estimated using extrapolation.

10. The method of claim 9, wherein the current temperature value is estimated using linear extrapolation.

11. The method of claim 6, wherein the current temperature value is estimated using polynomial extrapolation.

12. The method of claim 1, wherein the step of determining a bulk wavelength for each of the calibration temperature values comprises: defining a minimum wavelength value and a maximum wavelength value; and transmitting a plurality of light wavelengths between the minimum wavelength value and the maximum wavelength value to determine the bulk wavelength for each of the calibration temperature values.

13. The method of claim 12, further comprising the step of defining a wavelength step value, wherein the light wavelengths are transmitted between the minimum wavelength value and the maximum wavelength value by successively incrementing the transmitted wavelengths by an amount equal to the wavelength step value.

14. The method of claim 12, further comprising the step of creating a data set that includes a plurality of transmitted light wavelengths and a corresponding plurality of received light magnitudes measured by a detector.

15. The method of claim 14, wherein the bulk wavelength for each of the known calibration temperature values is determined by finding a peak magnitude value of the received light magnitudes.

16. The method of claim 14, wherein the bulk wavelength for each of the known calibration temperature values is determined by calculating a center of mass of the received light magnitudes within a bulk range.

17. The method of claim 16, wherein the bulk range is determined by identifying a maximum received light magnitude and determining a range of contiguous wavelengths for which the received light magnitudes are greater than the maximum received light magnitude minus a threshold value.

18. A method of estimating temperature comprising: selecting a plurality of known calibration temperature values; determining a bulk wavelength for each of the calibration temperature values by defining a minimum wavelength value and a maximum wavelength value and transmitting a plurality of light wavelengths between the minimum wavelength value and the maximum wavelength value; formulating a calibration data set of data points that includes the plurality of known temperature values and the corresponding plurality of bulk wavelengths; and using the calibration data set to determine an estimated current temperature value based upon a current bulk wavelength, wherein the current temperature value is estimated based upon one or more of the data points in the calibration data set.

19. The method of estimating temperature of claim 18, wherein the bulk wavelength for each of the known calibration temperature values is determined by calculating a center of mass of the received light magnitudes within a bulk range.

20. The method of claim 18, wherein the bulk wavelength for each of the known calibration temperature values is further determined by finding a peak magnitude value of a received light magnitude.

* * * * *